United States Patent [19]

Reynolds

[11] Patent Number: 4,878,840
[45] Date of Patent: Nov. 7, 1989

[54] ORTHODONTIC APPLIANCE

[75] Inventor: James M. Reynolds, Lubbock, Tex.

[73] Assignee: Zulauf, Inc., Lubbock, Tex.

[21] Appl. No.: 158,632

[22] Filed: Feb. 22, 1988

Related U.S. Application Data

[63] Continuation of Ser. No. 15,568, Feb. 13, 1987, which is a continuation of Ser. No. 625,075, Jun. 27, 1984, abandoned, which is a continuation of Ser. No. 506,404, Jun. 21, 1983, abandoned, which is a continuation of Ser. No. 355,137, Mar. 5, 1982, abandoned, which is a continuation of Ser. No. 135,652, Mar. 31, 1980, abandoned, which is a continuation of Ser. No. 930,577, Aug. 3, 1978, Pat. No. 4,216,583.

[51] Int. Cl.$^4$ .............................................. A61C 7/00
[52] U.S. Cl. .................................................... 433/9
[58] Field of Search ................................. 433/8, 9, 16

[56] References Cited

U.S. PATENT DOCUMENTS

| 1,083,769 | 9/1967 | Sandhaus . | |
| 1,516,079 | 6/1978 | Wiech . | |
| 3,085,336 | 4/1963 | Kesling | 433/14 |
| 3,178,821 | 4/1965 | Kesling | 433/14 |
| 3,250,000 | 5/1966 | Collito | 30/171 |
| 3,250,002 | 5/1966 | Collito | 433/217.1 |
| 3,345,745 | 10/1967 | Muller | 433/9 |
| 3,372,484 | 3/1968 | Mumaw | 433/2 |
| 3,504,438 | 4/1970 | Wittman et al. | 433/8 |
| 3,657,817 | 4/1972 | Kesling | 433/14 |
| 3,727,299 | 4/1973 | Hoffman et al. | 238/121 |
| 3,745,653 | 7/1973 | Cohl | 433/24 |
| 3,765,091 | 10/1973 | Northcutt | 433/9 |
| 3,775,850 | 12/1973 | Northcutt | 433/16 |
| 3,793,730 | 2/1974 | Begg et al. | 433/14 |
| 3,797,115 | 3/1974 | Silverman et al. | 433/8 |
| 3,874,080 | 4/1975 | Wallshein | 433/16 |
| 3,881,252 | 5/1975 | Andrews | 433/16 |
| 3,922,787 | 12/1975 | Fischer et al. | 433/15 |
| 3,964,165 | 6/1976 | Stahl | 433/8 |
| 4,107,844 | 8/1978 | Kurz | 433/9 |
| 4,155,964 | 5/1979 | Aronow | 264/13 |
| 4,197,118 | 4/1980 | Wiech, Jr. | 75/228 |
| 4,219,617 | 8/1980 | Wallshein | 433/8 |

Primary Examiner—Robert Peshock
Attorney, Agent, or Firm—Michael A. O'Neil

[57] ABSTRACT

An orthodontic appliance is molded either from a ceramic material or metal. When a ceramic material is used, the color of the appliance may be coordinated with that of a tooth. The appliance has a domed outwardly facing surface which is entirely curved in both the length and width directions and which is free of angular edge surfaces. The appliance may be adapted either for bonding directly to a tooth surface or for welding to a tooth encircling band. A cross slot extends into the body of the appliance, the cross slot having a curved surface between the bottom and sides of the cross slot.

11 Claims, 4 Drawing Sheets

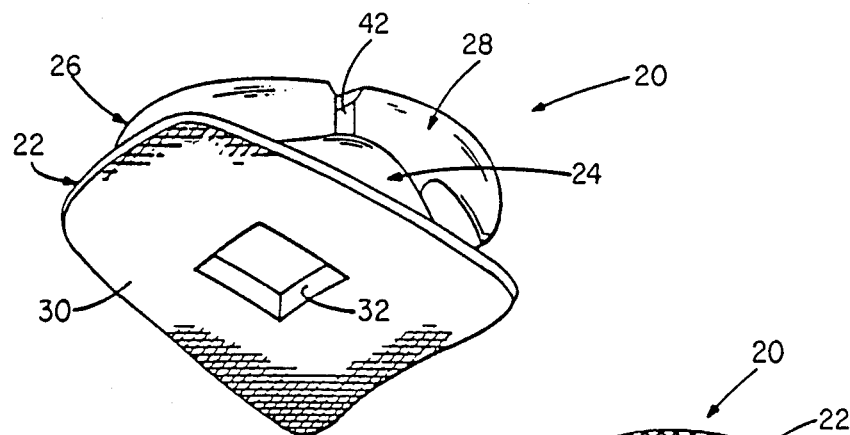
FIG. 6
FIG. 5
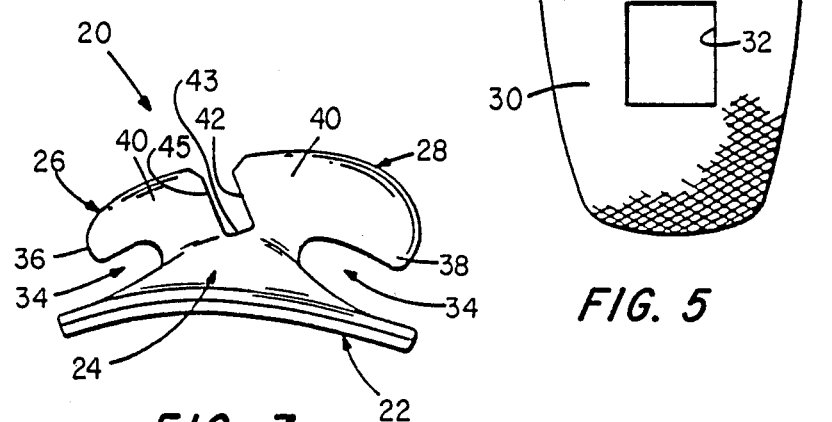
FIG. 7
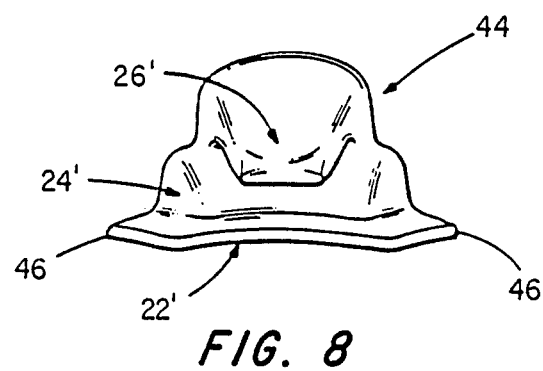
FIG. 8

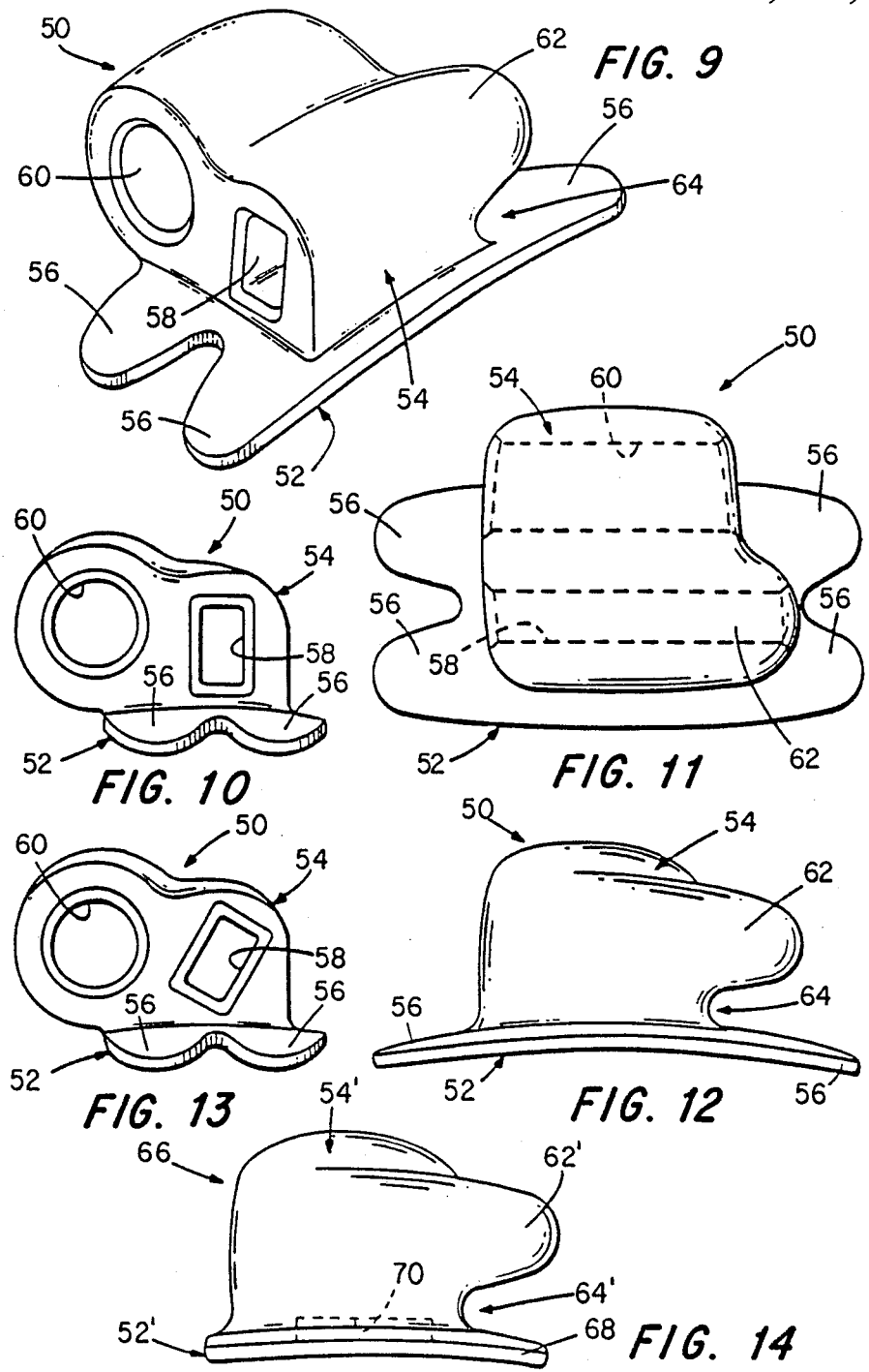

ORTHODONTIC APPLIANCE

CROSS REFERENCE TO RELATED APPLICATION

This application is a continuation of application Ser. No. 07/015,568, filed Feb. 13, 1987, which is in turn a continuation of application Ser. No. 06/625,075, filed June 27, 1984, now abandoned, which is in turn a continuation of Ser. No. 06/506,404, filed June 21, 1983, now abandoned, which is in turn a continuation of application Ser. No. 06/355,137, filed Mar. 5, 1982, now abandoned, which is in turn a continuation of application Ser. No. 06/135,652, filed Mar. 31, 1980, now abandoned, which was in turn a continuation of application Ser. No. 930,577, filed Aug. 3, 1978, now U.S. Pat. No. 4,216,583, issued Aug. 12, 1980.

TECHNICAL FIELD

This invention relates to orthodontic appliances, and more particularly to edgewise brackets and buccal tubes.

BACKGROUND AND SUMMARY OF THE INVENTION

Although the practice of orthodontics can be traced back at least to the time of the Egyptian mummies, modern developments in the art began in the 1920's when Dr. Edward Angle developed the first edgewise bracket. Such a bracket is for the purpose of connecting an orthodontic archwire to a tooth, as opposed to simply wrapping wires around the tooth and ligating to an activating archwire as had been the practice previously. Later on the so-called twin bracket was developed by Swain to permit the use of the bracket to apply a greater rotating and torquing force to the tooth. Still later developments included the Lewis gull wing bracket, the Steiner spring wing bracket, and the Lang stiff wing which incorporated a hole for ligating to rotate the tooth.

Brackets for orthodontic use were originally hand made from gold. In the late 1930's brackets machined from stainless steel were introduced. Stainless steel is generally satisfactory as an orthodontic bracket material, but prior to the present invention has presented numerous problems. First, it has heretofore been necessary to individually machine each bracket. This is costly, and also results in high angular edge surfaces which are very uncomfortable for the patient. Another difficulty involved the distinctive appearance of stainless steel, which many patients find objectionable.

In an attempt to overcome the foregoing and other difficulties, plastic orthodontic brackets were introduced. Plastic brackets can be fabricated so as to eliminate the angular edges of machined stainless steel brackets, and are therefore more comfortable for the patient. It is also possible to make plastic brackets in almost any desired color, including highly transparent brackets. It has been found in practice, however, that the use of polycarbonate plastic orthodontic brackets presents a different set of problems. First, plastic brackets are too weak to withstand desired torquing stresses, so that breakage and failure are not uncommon. Second, in the environment of the mouth plastic orthodontic brackets tend to rapidly discolor due to stains caused by various foods, tobacco, beverages such as tea and coffee, etc.

The present invention comprises improvements in the art of fabricating orthodontic appliances such as edgewise brackets, buccal tubes, and the like which overcome the foregoing and other difficulties long since associated with the prior art. In accordance with the broader aspects of the invention, orthodontic appliances are fabricated from either ceramic materials or metals utilizing an injection molding technique. Orthodontic appliances manufactured in accordance with the invention exhibit superior strength and toughness, are very comfortable for patients to use, are aesthetically pleasing, and do not stain or discolor in use.

Orthodontic appliances incorporating the invention are characterized by a domed outwardly facing surface. The domed outwardly facing surface is entirely curved in both the length and with dimensions, and is entirely free of angular edge surfaces.

In accordance with more specific aspects of the invention, orthodontic appliances may be fabricated from ceramic materials such as aluminum oxide. The color of each appliance can be made to correspond closely with the color of the tooth upon which the appliance will be used. Orthodontic appliances formed from ceramic materials are preferably adapted for bonding directly to the tooth surface. In such instances, the inwardly facing surface of the appliance may be scored to facilitate bonding, and may be provided with a noncircular aperture for receiving a quantity of bonding material and thereby preventing the appliance from rotating relative to the tooth, as the torquing forces are applied, via the rectangularly shaped wire.

DESCRIPTION OF THE DRAWINGS

A more complete understanding of the invention may be had by reference to the following Detailed Description when taken in conjunction with the accompanying Drawings, wherein:

FIG. 5 is a bottom view of the bracket shown in FIG. 1;

FIG. 6 is a bottom perspective view of the bracket shown in FIG. 1;

FIG. 7 is a view similar to FIG. 2 showing a modification of the first embodiment of the invention;

FIG. 8 is a view similar to FIG. 3 showing another modification of the first embodiment;

FIG. 9 is a perspective view of a buccal tube comprising a second embodiment of the invention;

FIG. 10 is an end view of the buccal tube of FIG. 9;

FIG. 11 is a stop view of the buccal tube of FIG. 10;

FIG. 12 is a side view of the buccal tube of FIG. 10;

FIG. 13 is a view similar to FIG. 10 illustrating a modification of the second embodiment of the invention;

FIG. 14 is a view similar to FIG. 12 illustrating another modification of the second embodiment;

DETAILED DESCRIPTION

Figure 1:
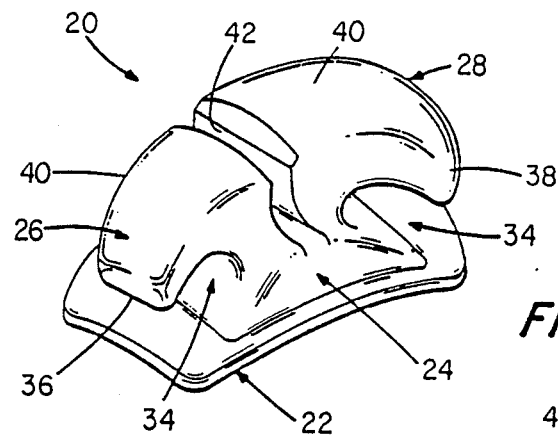
FIG. 1 is a perspective view of an edgewise bracket comprising the first embodiment of the invention.

Referring now to the Drawings, and particularly to FIG. 1 thereof, there is shown an orthodontic appliance 20 incorporating the first embodiment of the invention.

The orthodontic appliance 20 comprises an edgewise bracket formed from a ceramic material, preferably aluminum oxide. THe color of the bracket 20 is preferably selected to substantially match or otherwise conform to the color of the tooth upon which the bracket 20 will be used or to allow the color of the tooth to be visible through the bracket 20.

The bracket 20 comprises a unitary molded ceramic structure. The bracket 20 is preferably fabricated in accordance with the Wiech process, which involves mixing a particulate material, in this case aluminum oxide, with plasticizing and other ingredients, blending in accordance with appropriate physical and chemical procedures, molding the blended material to provide a shaped product, and then firing the shaped product to achieve the desired final dimensional and desired final physical property state. The assignee of the present application is the exclusive licensee for orthodontic appliances under the Wiech process, which is fully disclosed in application Ser. No. 262,851 filed by Raymond E. Wiech, Jr. on June 14, 1972, and the continuation thereof, application Ser. No. 676,194 filed by Raymond E. Wiech, Jr. on Apr. 12, 1976, the disclosures of which are incorporated herein by reference. Although a stain or coloring material may be added to the bracket prior to firing, the preferred technique is to stain or color the bracket after firing so that the color of the bracket is coordinated to correspond closely with the color of the tooth upon which the bracket is to be attached.

The bracket 20 comprises a base 22, a body 24 extending from the base 22, and wings 26 and 28 extending from the body 24. The bracket 20 is adapted for bonding directly to the tooth of a patient by means of bonding techniques which are well known in the art, for example, bonding techniques of the type disclosed in Muller U.S. Pat. No. 3,345,745 granted Oct. 10, 1967. As is best shown in FIGS. 5 and 6, the base 22 of the bracket 20 has an inwardly facing surface 30 which is preferably scored in a cross-sectional pattern so as to facilitate the adhesion thereof to the bonding agent. An aperture 32 is formed in the surface 30 of the base 22 to receive a mass of bonding material, thereby providing additional strength. The aperture 32 preferably has a substantially noncircular configuration so that the mass of bonding material received therein tends to resist forces tending to twist or turn the bracket 20 relative to the underlying tooth.

Figure 2:
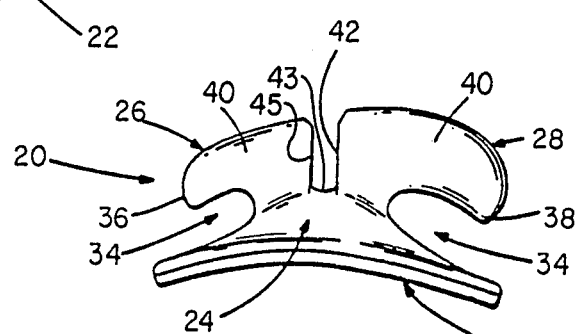
FIG. 2 is a side view of the bracket shown in FIG. 1.
Figure 3:
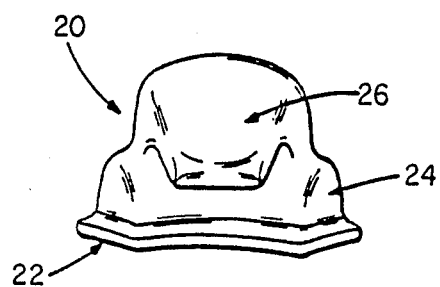
FIG. 3 is an end view of the bracket shown in FIG. 1.

Referring now to FIGS. 2 and 3, and body 24 of the bracket 20 is substantially equal in width to the base 22 thereof. However, the wings 26 and 28 are substantially narrower in width than either the base 22 or the body 24. As is best shown in FIG. 2, the body 24 of the bracket 20 is substantially shorter in length than the base 22. The wings 26 and 28 have a combined length which is substantially greater than that of the body 24, thereby providing a pair of wire receiving slots 34 extending between the wings 26 and 28 and the base 22. These slots are also designed to receive small plastic rings or modules used in binding an archwire to the bracket.

FIGS. 2 and 3 also illustrate an important feature of the invention comprising the outwardly facing domed surface of the bracket 20. The outwardly facing surface of the bracket engages the mouth tissue of the patient, and therefore the configuration of the outwardly facing surface is extremely important with respect to patient comfort. In accordance with the present invention, the outwardly facing surface of the bracket 20 is entirely curved in both the length and width directions. Of equal importance is the fact that the outwardly facing surface is entirely free of angular edges. In practice, it has been found that the outwardly facing surface of the bracket of the present invention comprises a substantial improvement in orthodontic appliances with respect to patient comfort.

Figure 4:
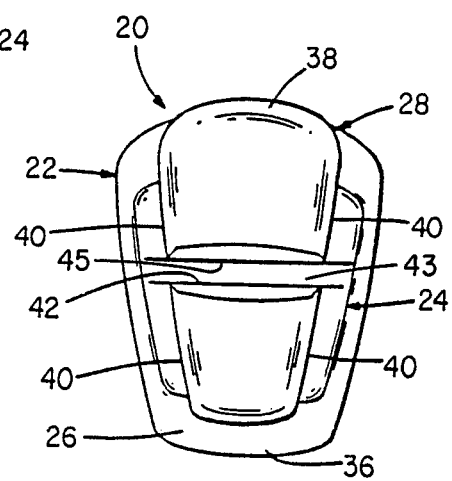
FIG. 4 is a top view of the bracket shown in FIG. 1.

Referring to FIG. 4, the wing 26 of the bracket 20 has relatively narrow incisal surface 36, and the wing 28 has a relatively wide gingival surface 38. The bracket 20 is always mounted with the incisal surface 36 facing the cutting edge of the tooth, that is, downwardly when the bracket 20 is mounted on an upper tooth and upwardly when the bracket 20 is mounted on a lower tooth. The wings 26 and 28 have side walls 40 tapered gradually from the relatively narrow incisal surface 36 to the relatively wide gingival surface 38. The wings 26 and 28 therefore provide generally a wedge shape extending from the incisal surface to the gingival surface, thereby causing food to move past the bracket 20 during patient chewing without applying undue force thereto.

Referring to FIG. 2, the slot 34 between the gingival wing 28 and the base 22 is substantially wider than the slot 34 between the incisal wing 26 and the base 22. This positions the undersurface of the wing 28 a substantial distance from the underlying tooth surface, thereby allowing for exuberent gingival tissue growth that often occurs as treatment progresses.

As is best shown in FIGS. 2 and 4, a slot 42 extends between the wings 26 and 28 and into the body 24 of the bracket 20. As is now common in the art of orthodontic appliances, the slot 42 is sized to matingly receive an archwire having predetermined dimensions. This facilitates precise registry of the bracket with the archwire, whereby the bracket may be utilized to apply force between the archwire and the tooth to which the bracket is attached.

The slot 42 has a bottom 43 and two sides 45. The surface of the slot 42 is curved between the bottom 43 and the sides 45 to avoid stress concentrations caused by sharp angles between surfaces. The rounded slot 42 is thus less likely to fracture.

FIG. 7 illustrates a modification of the first embodiment of the invention wherein the slot 42 extends angularly. It will be understood that the slot 42 may have any desired orientation with respect to the remaining components of the bracket 20. The slot 42 may also be angulated with respect to the length of the bracket.

In FIG. 8 there is shown an edgewise bracket 44 comprising a further modification of the first embodiment of the invention. The bracket 44 includes numerous component parts which are substantially identical in construction and function to component parts of the bracket 20 illustrated in FIGS. 1 through 6, and such identical component parts are designated in FIG. 8 with the same reference numerals utilized hereinbefore in the description of the bracket 20, but are differentiated therefrom by means of a prime (') designation.

The bracket 44 is similar to the bracket 20 in that it is fabricated by means of the above-described Wiech process. The primary difference between the bracket 44 and the bracket 20 involves the fact that the bracket 44 is formed from a metal, such as stainless steel. Although ceramic materials are generally considered preferable for the fabrication of edgewise brackets, primarily due to the capability of coordinating the color of ceramic brackets with the color of the underlying tooth, the use of metal edgewise brackets may be considered preferable in some instances. In particular, the use of metal may be considered preferable in those instances in which it is necessary or desirable to attach the bracket to a tooth encircling band. For this reason, the bracket 44 is provided with extensions 46 on the opposite ends of the base 22 to facilitate the welding of the bracket 44 to a tooth encircling band, or a steel disc with a convex under side that is suitable for bonding to the tooth surface. Another manufacturing technique involves forming the bracket from a first metal using the Wiech process, and subsequently infusing or plating the formed bracket with another metal. For example, brackets formed from plain carbon steel by means of the above-described Wiech process and subsequently infused with stainless steel to a depth of about 3 millimeters by means of the Dilex process have proven satisfactory in actual practice.

Referring now to FIG. 9, there is shown an orthodontic appliance 50 comprising a second embodiment of the invention. The appliance 50 comprises a double buccal or terminal tube, it being understood that the invention is equally applicable to single, double, or triple buccal or terminal tubes. A single buccal or terminal tube has a single passageway therethrough, a double buccal or terminal tube has two passageways therethrough and a triple buccal or terminal tube has three passageways therethrough. These passageways may be shaped to accept an archwire, a cervical retractor or any other desired member as needed during treatment. The buccal tube 50 is preferably formed from stainless steel in accordance with the above-described Wiech process.

The buccal tube 50 comprises a base 52 and a body 54 extending from the base 52. Base 52 is greater in length than the body 54, primarily to provide a plurality of flanges 56. The purpose of the flanges 56 is to facilitate the welding of the buccal tube 50 to an underlying tooth encircling band.

As is best shown in FIGS. 10 and 11, the body 54 of the buccal tube 50 is substantially equal in width to the base 52 thereof. However, the body 54 projects outwardly from one side of the buccal tube 50, and the base 52 projects outwardly from the opposite side. The body 54 has a rectangular passageway 58 formed therethrough which is sized to matingly receive an archwire having predetermined dimensions. The body 54 also has formed therethrough a passageway 60 which is sized to matingly receive a cervical retractor of predetermined dimensions.

As is best shown in FIGS. 11 and 12, the body 54 of the buccal tube 50 has a portion 62 extending beyond the remainder thereof. A tie back slot 64 extends between the portion 62 of the body 54 and the base 52. By this means a wire may be connected between the archwire extending through the passageway 58 and tie back slot 54 of the buccal tube 50, which in turn facilitates the application of force between the archwire and the tooth underlying the buccal tube 50.

Referring particularly to FIGS. 10 and 12, the buccal tube 50 has a domed outwardly facing surface. That is, the outwardly facing surface of the buccal tube 50 is entirely curved in both the length and width directions. Of equal importance is the fact that the outwardly facing surface of the buccal tube 50 is entirely free of any angular edge surfaces. In practice it has been found that the use of a domed outwardly facing surface in the buccal tube 50 is highly important in substantially increasing the comfort to patients requiring the buccal tube.

Referring to FIG. 13, there is shown a buccal tube 50 comprising a modification of the second embodiment of the invention. The buccal tube 50 of FIG. 13 is identical in all aspects to the buccal tube 50 shown in FIGS. 9 through 12, but differs therefrom in that the passageway 58 extends angularly with respect to the bottom surface of the buccal tube. This is to facilitate those applications in which it is necessary or desirable to exert a twisting force against the underlying tooth from the archwire through the buccal tube. It will be understood that the passageway 58 may extend at any desired angle in accordance with the particular requirements.

Referring to FIG. 14, there is shown a buccal tube 66 comprising the further modification of the second embodiment of the invention. The buccal tube 66 includes numerous component parts which are substantially identical in construction and function to component parts of the buccal tube 50 as described hereinabove in connection with FIGS. 9 through 12. Such identical component parts are designated in FIG. 14 by means of the same reference numerals utilized in connection with the description of the buccal tube 50, but are differentiated therefrom by means of a prime (') designation.

Like the buccal tube 50, the buccal tube 66 is formed by means of the Wiech process. The primary differentiation between the buccal tube 66 and the buccal tube 50 involves the fact that the buccal tube 66 is formed from a ceramic material, for example, aluminum oxide. This permits the color of the buccal tube 66 to be coordinated with the color of the underlying tooth.

Since buccal tubes formed from ceramic materials are not readily weldable, the base 52' of the buccal tube 66 is shortened to eliminate the flanges 56 of the buccal tube 50. The inwardly facing surface 68 of the buccal tube 66 is stored in a cross-hatch pattern so as to facilitate the adhesion thereof to a bonding agent. Also, the surface 68 is provided with an aperture 70 to receive a mass of bonding agent and thereby providing additional strength. The aperture 70 is preferably provided with a substantially noncircular or even rectangular configuration and thereby resists forces tending to twist or turn the buccal tube 66 relative to the underlying tooth.

Figure 15:
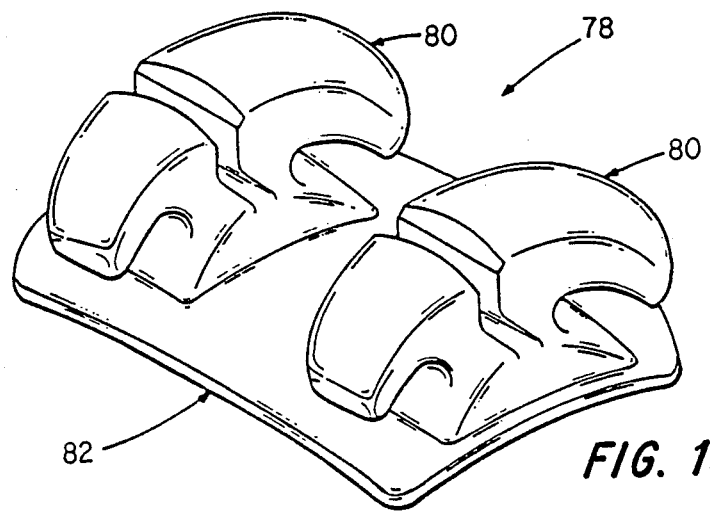
FIG. 15 is a perspective view of a bracket comprising a third embodiment of the invention.
Figure 16:
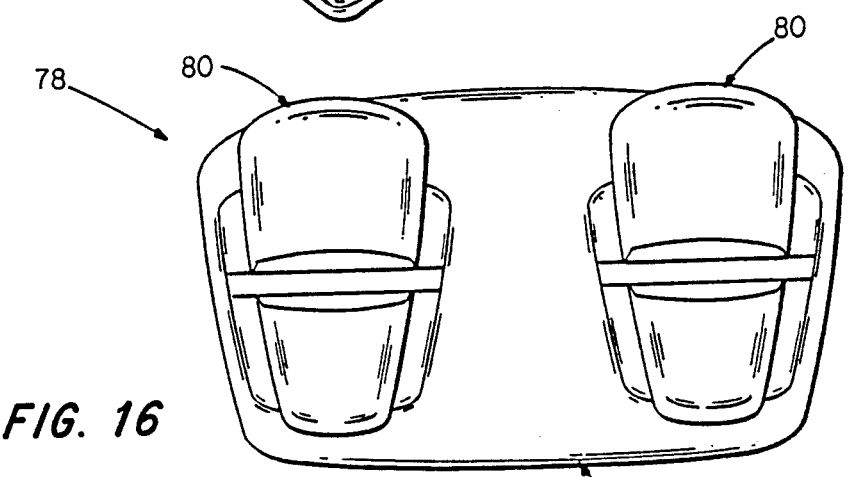
FIG. 16 is a top view of the bracket of FIG. 15.
Figure 17:
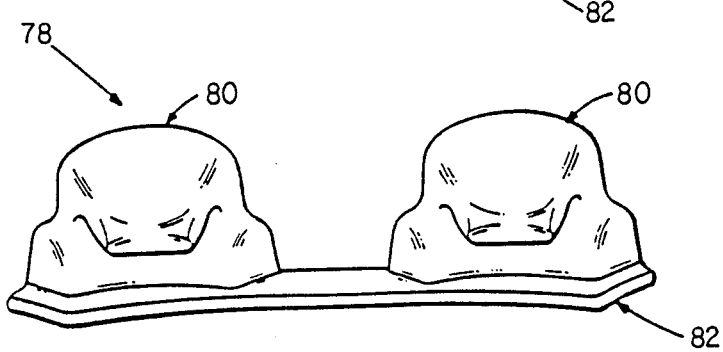
FIG. 17 is an end view of the bracket of FIG. 15.

Referring to FIGS. 15, 16 and 17, there is shown a bracket 78 comprising a third embodiment of the invention. The bracket 78 comprises a pair of bracket portions 80 each of which is substantially identical to the bracket 20 described hereinabove in connection with FIGS. 1-6. The bracket portions 80 are interconnected by a common base 82 which serves to maintain the bracket portions 80 in a predetermined spaced apart relationship.

The bracket 78 functions similarly to the twin brackets which are currently in use. By means of the bracket 78, an increased torque can be applied to the tooth, whereby the force tending to rotate the tooth is substantially increased.

The bracket 78 is preferably formed by means of the above-described Wiech process. The bracket 78 may be formed form a ceramic material such as aluminum oxide in which case the color of the bracket may be substantially matched to the color of the underlying tooth. Ceramic brackets are preferably secured directly to the tooth surface. The bracket 78 may also be fabricated from stainless steel, in which case the bracket is adapted for welding to a tooth encircling band. Alternatively, the bracket may be formed from plain carbon steel utilizing the Wiech process, after which stainless steel may be infused into the material of the bracket utilizing the Dilex process.

Although particular embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

I claim:

1. An orthodontic appliance comprising:
   a base having an inwardly facing surface on one side thereof adapted for attaching the appliance and a body portion extending outwardly from the other side of said base;
   said body portion having one embodiment substantially shorter than a corresponding dimension of the base;
   a pair of wings, each wing extending in opposite directions from the body portion and having a length extending substantially beyond the body portion to define wire receiving slots between the base and the ends of said wings;
   the wings defining an outwardly facing domed surface which is curved in at least one direction and which thereby presents a comfortable surface to the mouth tissue of the patient; and
   a cross slot extending into said body portion between the wings and configured to receive therein a dental appliance of predetermined dimensions, the cross slot having a curved surface between the bottom of the cross slot and the sides of the cross slot to reduce stress concentrations.

2. The orthodontic appliance according to claim 1 wherein the inner surface of the base is adapted for bonding directly to the tooth of a patient, and further including an aperture formed in the inner surface of the base for receiving a quantity of bonding material.

3. The orthodontic appliance according to claim 2 wherein the aperture in the base has a substantially noncircular configuration and thereby serves to prevent rotation of the appliance relative to the tooth.

4. The orthodontic appliance according to claim 1 wherein the width of the body is substantially equal to the width of the base and the width of the wings is substantially narrower than the width of the base.

5. The orthodontic appliance according to claim 1 wherein the entire appliance comprises a unitary molded structure formed from a material selected from the group including ceramics and metals.

6. The orthodontic appliance according to claim 5 wherein the appliance is formed from aluminum oxide.

7. The orthodontic appliance according to claim 6 wherein the appliance has a color coordinated with the color of a tooth.

8. An orthodontic appliance comprising:
   a base having an inwardly facing surface on one side thereof contoured for bonding directly to the tooth of a patient;
   said base including a body portion extending from the other side of the base, the body portion having a length substantially shorter than the length of the base and a width substantially equal to the width of the base;
   a wing extending in each of opposite directions from the body portion, each wing having a length extending substantially beyond the length of the body to define wire receiving slots between the base and the ends of said wings;
   the wings defining an outwardly facing dome surface which is generally curved in at least one direction and which thereby presents a comfortable surface to mouth tissues;
   a cross slot extending into said body portion between the wings and configured to receive therein a dental appliance of predetermined dimension, the cross slot having a curved surface between the bottom of the cross slot and the sides of the cross slot; and
   the entire appliance comprising a unitary, molded structure.

9. The orthodontic appliance according to claim 8 wherein the appliance is transparent to allow the color of a tooth to be visible through the appliance so as to cause the appliance to be substantially inconspicuous to the eye.

10. The orthodontic appliance according to claim 8 wherein the appliance is formed from aluminum oxide.

11. The orthodontic appliance according to claim 16 wherein the appliance is colored in accordance with the color of a tooth.

* * * * *

UNITED STATES PATENT AND TRADEMARK OFFICE
CERTIFICATE OF CORRECTION

PATENT NO. : 4,878,840
DATED : November 7, 1989
INVENTOR(S) : James M. Reynolds

It is certified that error appears in the above-identified patent and that said Letters Patent is hereby corrected as shown below:

Column 2, line 14, "with" should be --width--.

Column 3, line 40, "cross-sectional" should be --cross-hatched--.

Column 7, line 18, "one embodiment" should be --one dimension--.

Column 8, line 44, "Claim 16" should be --Claim 10--.

Signed and Sealed this

Fifth Day of February, 1991

Attest:

HARRY F. MANBECK, JR.

*Attesting Officer*     *Commissioner of Patents and Trademarks*

REEXAMINATION CERTIFICATE (2597th)

United States Patent [19]

Reynolds

[11] B1 4,878,840

[45] Certificate Issued Jun. 13, 1995

[54] ORTHODONTIC APPLIANCE

[75] Inventor: James M. Reynolds, Lubbock, Tex.

[73] Assignee: Class One Orthodontics, Inc.

Reexamination Requests:
No. 90/002,998, Mar. 17, 1993
No. 90/003,084, Jun. 4, 1993

Reexamination Certificate for:
Patent No.: 4,878,840
Issued: Nov. 7, 1989
Appl. No.: 158,632
Filed: Feb. 22, 1988

Certificate of Correction issued Feb. 5, 1991.

Related U.S. Application Data

[63] Continuation of Ser. No. 15,568, Feb. 13, 1987, which is a continuation of Ser. No. 625,075, Jun. 27, 1984, abandoned, which is a continuation of Ser. No. 506,404, Jun. 21, 1983, abandoned, which is a continuation of Ser. No. 355,137, Mar. 5, 1982, abandoned, which is a continuation of Ser. No. 135,652, Mar. 31, 1980, abandoned, which is a continuation of Ser. No. 930,577, Aug. 3, 1978, Pat. No. 4,216,583.

[51] Int. Cl.⁶ ............................ A61C 3/00; A61C 7/00
[52] U.S. Cl. ...................................................... 433/9
[58] Field of Search ................................ 433/8, 9, 16

[56] References Cited

U.S. PATENT DOCUMENTS

| | | | |
|---|---|---|---|
| 3,085,336 | 4/1963 | Kesling | 433/14 |
| 3,178,821 | 4/1965 | Kesling | 433/14 |
| 3,250,000 | 5/1966 | Collito | 30/171 |
| 3,250,002 | 5/1966 | Collito | 433/217.1 |
| 3,835,538 | 9/1974 | Northcutt | 433/9 |
| 3,923,940 | 1/1976 | Andren | 433/9 |
| 4,050,156 | 9/1977 | Chasanoff et al. | 433/8 |
| 4,219,617 | 8/1980 | Wallshein | 433/8 |

OTHER PUBLICATIONS

Unitek, Orthodontic Materials Catalog, 1975.
TP Orthodontics, "Straight-Talk", 1977.
Ormco, Catalog listing for "Wedge Bracket", 1976.
Zulauf, Price List for "Smoothie" Bracket, 1976.

*Primary Examiner*—Nicholas D. Lucchesi

[57] ABSTRACT

An orthodontic appliance is molded either from a ceramic material or metal. When a ceramic material is used, the color of the appliance may be coordinated with that of a tooth. The appliance has a domed outwardly facing surface which is entirely curved in both the length and width directions and which is free of angular edge surfaces. The appliance may be adapted either for bonding directly to a tooth surface or for welding to a tooth encircling band. A cross slot extends into the body of the appliance, the cross slot having a curved surface between the bottom and side of the cross slot.

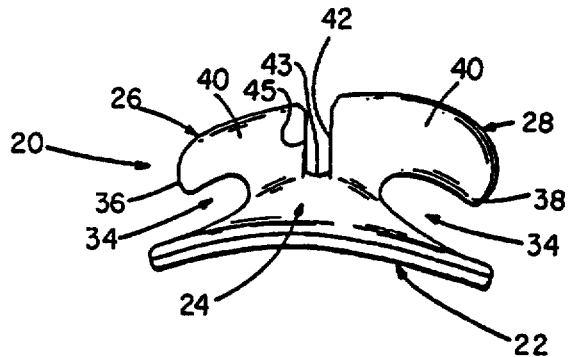

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 10 is cancelled.

Claims 1, 5, 8, 11 are determined to be patentable as amended.

Claims 2-4, 6, 7, 9, dependent on an amended claim, are determined to be patentable.

New claim 12 is added and determined to be patentable.

1. An orthodontic appliance comprising:
a base having an inwardly facing surface on one side thereof adapted for attaching the appliance and a body portion extending outwardly from the other side of said base;
said body portion having one embodiment substantially shorter than a corresponding dimension of the base;
a pair of wings, each wing extending in opposite directions from the body portion and having a length extending substantially beyond the body portion to define wire receiving slots between the base and the ends of said wings;
the wings defining an outwardly facing domed surface which is curved in at least one direction and which thereby presents a comfortable surface to the mouth tissue of the patient; [and]
a cross slot extending into said body portion between the wings and configured to receive therein a dental appliance of predetermined dimensions, the cross slot having a curved surface between the bottom of the cross slot and the sides of the cross slot to reduce stress concentrations; *and*
*wherein said appliance is formed of a ceramic material.*

5. The orthodontic appliance according to claim 1 wherein the entire appliance comprises a unitary molded structure [formed from a material selected from the group including ceramics and metals].

8. An orthodontic appliance comprising:
a base having an inwardly facing surface on one side thereof contoured for bonding directly to the tooth of a patient;
said base including a body portion extending from the other side of the base, the body portion having a length substantially shorter than the length of the base and a width substantially equal to the width of the base;
a wing extending in each of opposite directions from the body portion, each wing having a length extending substantially beyond the length of the body to define wire receiving slots between the base and the ends of said wings;
the wings defining an outwardly facing domed surface which is generally curved in at least one direction and which thereby presents a comfortable surface to mouth tissues;
a cross slot extending into said body portion between the wings and configured to receive therein a dental appliance of predetermined dimension, the cross slot having a curved surface between the bottom of the cross slot and the sides of the cross slot; and
the entire appliance comprising a unitary, molded structure *formed of aluminum oxide.*

11. The orthodontic appliance according to claim [10] *8* wherein the appliance is colored in accordance with the color of a tooth.

*12. An orthodontic appliance comprising:*
*a base having an inwardly facing surface on one side thereof adapted for attaching the appliance and a body portion extending outwardly from the other side of said base;*
*said body portion having one dimension substantially shorter than a corresponding dimension of the base;*
*a pair of wings, each wing extending in opposite directions from the body portion and having a length extending substantially beyond the body portion to define wire receiving slots between the base and the ends of said wings;*
*the wings defining an outwardly facing domed surface which is curved in at least one direction and which thereby presents a comfortable surface to the mouth tissue of the patient;*
*a cross slot extending into said body portion between the wings and configured to receive therein a dental appliance of predetermined dimensions, the cross slot having a curved surface between the bottom of the cross slot and the sides of the cross slot to reduce stress concentrations, and*
*wherein said appliance is made from a composition comprising $Al_2O_3$.*

* * * * *